United States Patent [19]

Dowdy

[11] Patent Number: 5,042,507

[45] Date of Patent: Aug. 27, 1991

[54] SURGICAL DRAPE FOR OPHTHALMIC PROCEDURES

[75] Inventor: Richard C. Dowdy, Valencia, Calif.

[73] Assignee: Baxter International Inc., Deerfield, Ill.

[21] Appl. No.: 482,622

[22] Filed: Feb. 21, 1990

[51] Int. Cl.$^5$ ............................................. A61B 19/08
[52] U.S. Cl. .................................. 128/849; 128/853; 128/857
[58] Field of Search ............... 128/849, 852, 853, 854, 128/857

[56] References Cited

U.S. PATENT DOCUMENTS

| | | | |
|---|---|---|---|
| 3,667,458 | 6/1972 | Krebs | 128/853 |
| 3,791,382 | 2/1974 | Collins | 128/853 |
| 3,800,790 | 4/1974 | Collins | 128/854 |
| 3,826,253 | 7/1974 | Larsh et al. | 128/854 |
| 3,902,484 | 9/1975 | Winters | 128/849 |
| 3,911,912 | 10/1975 | Krebs et al. | 128/849 |
| 3,916,887 | 11/1975 | Kelly | 128/851 |
| 3,923,052 | 12/1975 | Zoephel | 128/853 |
| 3,952,738 | 4/1976 | Krzewinski | 564/443 |
| 3,955,569 | 5/1976 | Krzewinski et al. | 128/855 |
| 4,166,461 | 9/1979 | Oliver et al. | 128/855 |
| 4,169,472 | 10/1979 | Morris | 128/854 |
| 4,275,720 | 6/1981 | Wichman | 128/853 |
| 4,323,062 | 4/1982 | Canty | 128/852 |
| 4,378,794 | 4/1983 | Collins | 128/853 |
| 4,457,026 | 7/1984 | Morris | 2/171 |
| 4,462,396 | 7/1984 | Wichman | 128/853 |
| 4,476,860 | 10/1984 | Collins et al. | 128/853 |
| 4,489,720 | 12/1984 | Morris et al. | 128/853 |
| 4,890,628 | 1/1990 | Jackson | 128/849 |

Primary Examiner—Robert A. Hafer
Assistant Examiner—Kevin G. Rooney
Attorney, Agent, or Firm—Kay H. Pierce; Paul C. Flattery

[57] ABSTRACT

A surgical drape including a fluid collection trough integrally formed therein. In an embodiment, the fluid collection trough is positioned to fit between a patient's head and a wrist rest positioned about the head. The drape preferably includes a head covering portion incorporating the collection trough that preferably is made of a translucent plastic film so as to permit viewing of a patient's head. The trough preferably is contoured to include a lower portion in which fluid collects.

5 Claims, 2 Drawing Sheets

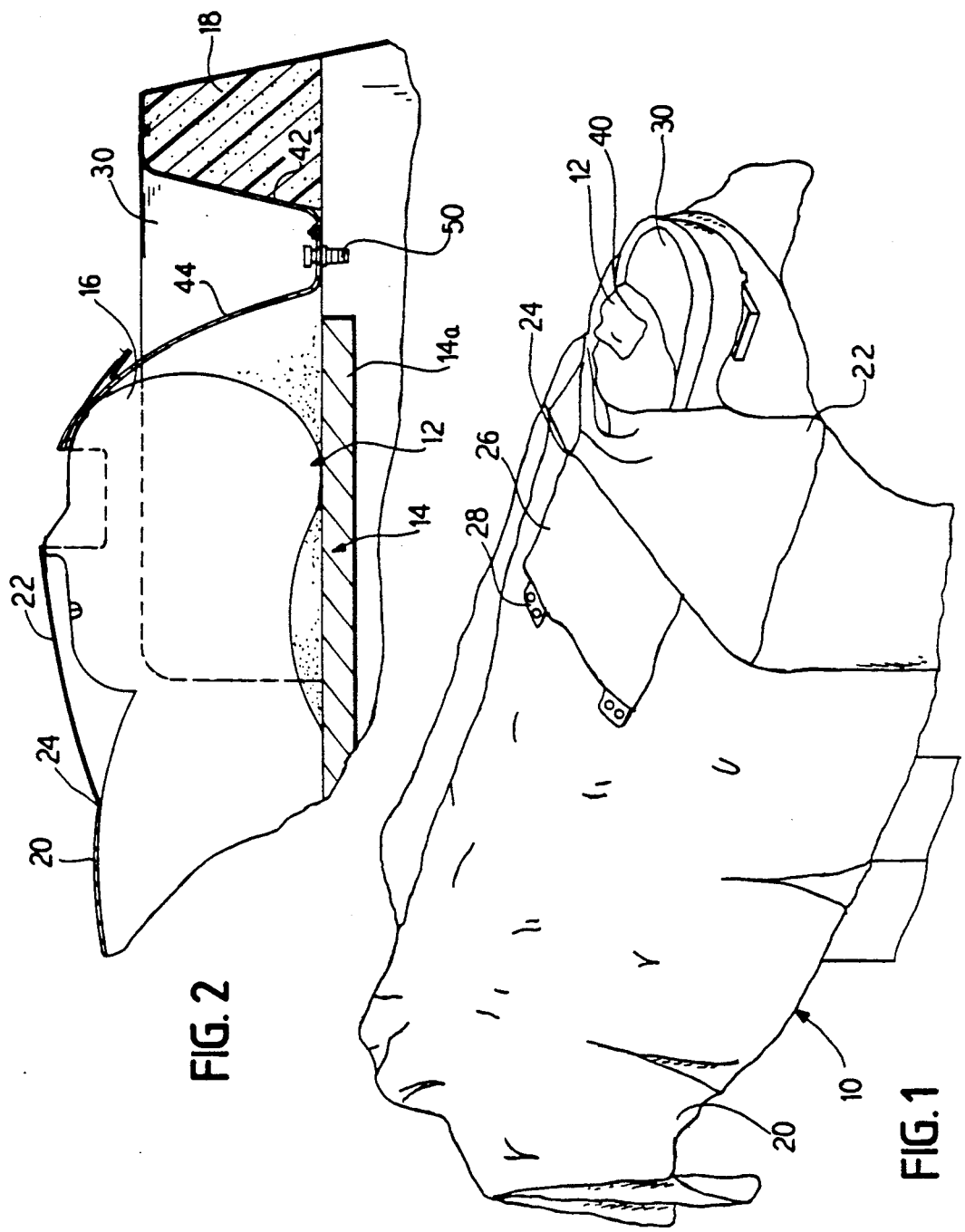

SURGICAL DRAPE FOR OPHTHALMIC PROCEDURES

BACKGROUND OF THE INVENTION

The present invention generally relates to surgical drapes. More specifically, the present invention relates to surgical drapes for ophthalmic procedures.

Surgical drapes are utilized during surgical procedures to cover at least portions of a patient. There are a variety of such surgical drapes, some of which are designed for specific surgical procedures. For example, presently, there are a number of surgical drapes designed for ophthalmic procedures. These drapes are either disposable and comprise a non-woven synthetic material or reusable and comprise a woven material. These drapes generally consist of a base sheet with a fenestrated split to allow for draping around a patient's head.

U.S. Pat. No. 3,910,268 relates to a surgical drape including a flap attached to a base sheet so as to create a gap for an operative site. U.S. Pat. No. 3,952,738 relates to a surgical drape with a split fenestration used in combination with a bar drape for draping ophthalmic procedures.

In utilizing each of the drapes set forth in each of the above-identified patents, during an ophthalmic procedure, a disposable plastic incise drape is placed over a patient's head and the eye on which a procedure is to be performed. During ophthalmic procedures, fluids are generated, due to, e.g. irrigation fluids and eye drops, that must be controlled and disposed of. Typically, to control and channel these fluids, the ends of the incise drape are folded and placed into a fluid collection pouch that is attached to the drape.

Other methods are utilized for controlling fluids generated during surgical procedures, such as ophthalmic procedures. These methods, however, require the use of multiple components. For example, it is known, in ophthalmic procedures, to utilize an eyewick that channels fluids from the eye, on which the operative procedure is being performed. It is also known to use direct fluid aspiration.

All of the above-disclosed drapes and procedures, for controlling fluid, require the utilization of secondary drapes and ancillary items. These secondary drapes and ancillary items are typically cumbersome and can be time consuming to assemble. Further, there is the risk of cross-contamination because of the handling of a plurality of products in an attempt to create a sterile field.

SUMMARY OF THE INVENTION

The present invention discloses a complete one-drape draping system that provides a sterile operative field and complete fluid control for ophthalmic procedures. Utilizing the drape of the present invention, the risk of cross-contamination is reduced because the present invention eliminates the need to handle a plurality of draping products in order to control fluids.

To this end, in an embodiment, the present invention provides a surgical drape having a fluid collection trough incorporated therein. The fluid collection trough is located between a patient's head and a wrist rest surrounding the head.

In another embodiment of the present invention, a drape is provided that includes a major base sheet portion to which is attached a minor head covering sheet portion that includes a fluid collection trough.

In another embodiment of the present invention, a surgical drape is provided wherein the fluid collection trough is contoured to define a lower portion for collecting fluid.

In another embodiment of the present invention, the collection trough includes a suction nozzle positioned at a lower portion of the trough.

In another embodiment of the present invention, a surgical drape is provided having a head covering portion that is constructed of a translucent plastic film. The translucent plastic film allows a surgeon or other personnel, such as an anesthesiologist, to view and monitor the patient.

In another embodiment of the present invention, the surgical drape includes an adhesively backed incise area. The incise area can be placed about an operative site. In an embodiment, the adhesively backed incise area is part of the minor sheet portion.

Accordingly, an advantage of the present invention is to provide an improved surgical drape.

Furthermore, an advantage of the present invention is to provide a surgical drape wherein only a single drape is required to perform an ophthalmic procedure.

Another advantage of the present invention is that it reduces the risk of cross-contamination because only one draping product is required.

A further advantage of the present invention is that the drape provides the ability to view a patient's face, and thereby monitor a patient's skin color and the like, during the surgical procedure.

Moreover, another advantage of the present invention is that it provides a seal around the operative site by means of an adhesively backed incise area which provides for fluid run-off.

Additional features and advantages of the present invention are described in, and will be apparent from, the detailed description of the presently preferred embodiments and from the drawings.

BRIEF DESCRIPTION OF THE DRAWINGS

FIG. 1 is a perspective view of an embodiment of the surgical drape of the present invention.

FIG. 2 is a cross-sectional view of the surgical drape of FIG. 1.

DETAILED DESCRIPTION OF THE PRESENTLY PREFERRED EMBODIMENTS

Figure 3:
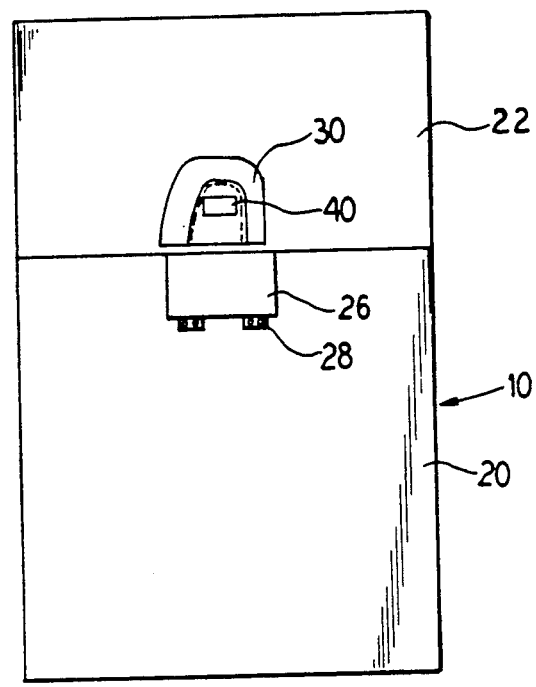
FIG. 3 is a plan view of the surgical drape of FIG. 1.

The present invention provides a surgical drape that provides a sterile operative field and a contoured pouch for fluid collection and control. The surgical drape of the present invention is particularly adapted for use in ophthalmic procedures. However, the surgical drape can be used in other surgical procedures.

Referring now to the figures, and specifically FIGS. 1 and 2, an embodiment of the surgical drape 10 of the present invention is illustrated. As illustrated, the surgical drape 10 is designed to be draped about a patient 12 who is positioned on an operating table 14. In the embodiment of the present invention illustrated, the patient 12 has been prepared for an ophthalmic procedure. Accordingly, the patient's head 16 is positioned on an extension 14a and is surrounded by a wrist rest 18. As is well-known in the art, the wrist rest 18 provides the surgeon performing the operative procedure with a support on which he can rest his hands, preferably horizontally, while performing the surgery. Typically, the wrist rest 18 is U-shaped or horseshoe-shaped, as illustrated.

The surgical drape 10, of the present invention, includes a major/base sheet portion 20 to which is attached a minor/head covering or upper sheet portion 22. The major sheet portion 20 and the minor sheet portion 22 are joined at a seam 24 to define the surgical drape 10. As illustrated, the major sheet portion 20 and minor sheet portion 22 function to cover the patient during a surgical procedure.

Attached to the major sheet portion 20 and extending from the seam 24 is an instrument pad 26. In the embodiment of the surgical drape 10 illustrated, a plurality of tube or cord holders 28 are attached to the instrument pad 26. The instrument pad 26 functions to not only secure tubes to the drape 10, but also functions to provide an area on which surgical tools and the like can be positioned. Accordingly, preferably, the instrument pad 26 is constructed from a non-skid material, for example polyurethane foam, and is of a size suitable for receiving tools thereon. The instrument pad 26 can be affixed to the major sheet portion 20 by means of a suitable adhesive or the like.

The major sheet portion 20 preferably is rectangular or square in shape. The major sheet portion 20, of the surgical drape 10, should be of sufficient size to cover at least a majority of the patient's body, excluding the head and neck region. In a preferred embodiment, it has been found that if the major sheet portion 20 has a size of approximately 77 inches by 77 inches, it functions satisfactorily. The major sheet 20 preferably is made of a non-woven fabric.

As illustrated, the minor sheet portion 22 includes a fluid collection trough 30. Preferably, the fluid collection trough 30 is located at a position between the patient's head 16 and the wrist rest 18. The fluid collection trough 30 functions to collect fluid, such as irrigation fluid, that flows either from or over the face of the patient during the surgical procedure. The fluid collection trough 30 is discussed in more detail hereinafter.

Additionally, in the embodiment of the surgical drape 10 illustrated, the minor sheet portion 22 includes a fenestration or window 40 that is constructed so that it registers about the eyes of the patient 12 during the surgical procedure. The fenestration 40 provides an area through which an operative procedure can be performed.

The minor sheet portion 22 preferably has a rectangular or square shape. The minor sheet portion 22 should be of a size sufficient to cover at least the head and neck regions of the patient. It has been found that a minor sheet portion 22 measuring approximately 35 inches by 77 inches functions satisfactorily.

The minor sheet portion 22 preferably is made of a translucent plastic film such as, for example, polyethylene, and includes an embossed matte. The translucent nature of the minor sheet portion 22 allows the patient's head to be viewed by surgical personnel, for example, the anesthesiologist, during the surgical procedure. The embossing characteristics eliminate glare but still enables visualization of a patient's head through the minor sheet portion 22. For procedures during which only a local anesthetic is required, such as a cataract procedure, the translucent nature of the film prevents the patient from viewing instruments that are directed at a patient's eyes. This results in greater patient comfort and less patient anxiety.

As previously stated, the minor sheet portion 22 includes a trough 30 designed to surround at least a portion of the patient's head during the surgical procedure. The trough 30 functions to collect fluid, such as irrigation fluid or the like, generated during the surgical procedure. The trough 30 has a contoured pouch-like construction.

Figure 4:
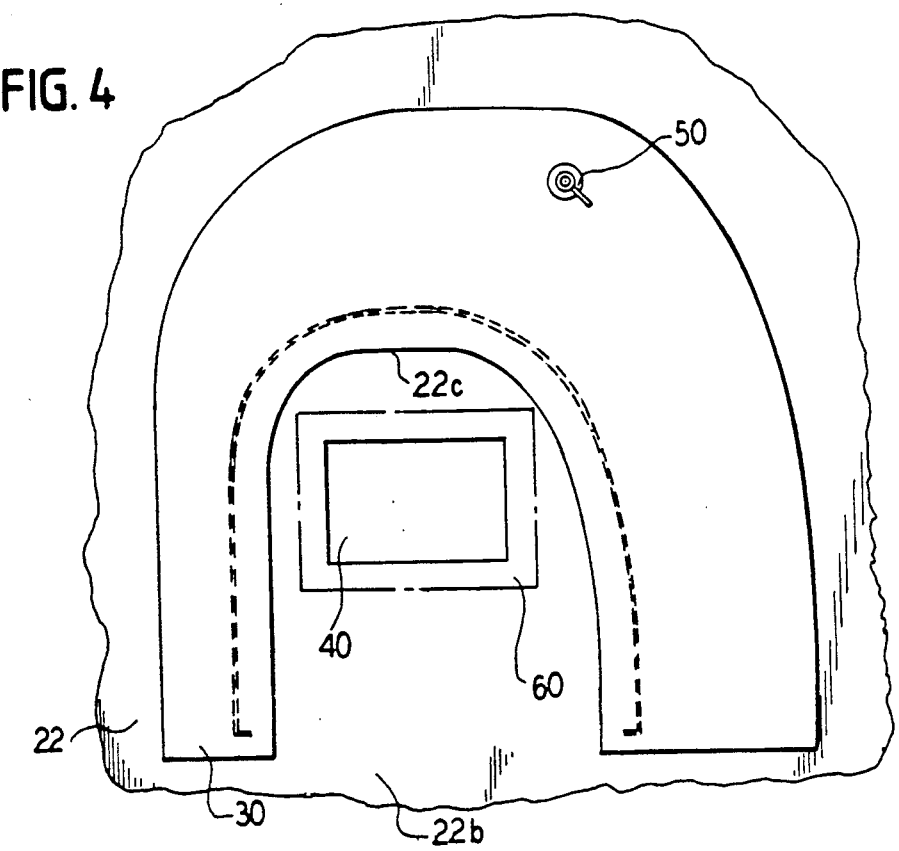
FIG. 4 is a partial plan view of an underside of the surgical drape of FIG. 1.

Referring to FIGS. 2 and 4, the trough 30 is preferably formed from the same material as the minor sheet portion 22, for example, a web of plastic material such as polyethylene. The trough 30 is formed so that it extends downwardly, when the surgical drape is secured over the patient, from a plane defined by the minor sheet portion 22. The trough 30 is formed so that it includes a lower portion, that extends further downwardly from the plane of the sheet than other portions of the trough. Fluid will collect in this lower portion of the trough 30.

Preferably, the trough 30 includes a port or nozzle 50. The port is preferably attached to the trough 30, at approximately the lowest point in the trough 30 wherein fluid collects. Accordingly, the port 50 provides an outlet through which fluid collected in the trough 30 can be extracted. The fluid can be extracted either via gravity induced drainage or by an appropriately attached suction line.

As illustrated in FIG. 2, the trough 30 is secured to remaining portions of the minor sheet portion 22 by being received within a slit in the minor sheet portion 22. The slit has a shape that conforms to the shape of the inner periphery of the trough 30. As a result, a tab section 22b, having a convex periphery 22c, is formed in the minor sheet portion 22. The outer peripheries of the trough 30, that are defined by two gusset members 42 and 44, are attached to the minor sheet portion 22 by heat sealing or other means. Of course, if desired, the trough 30 can be created integral with the minor sheet portion 22.

As illustrated in FIGS. 1 and 2, when the drape 10 is positioned over the patient 12, the trough 30 is located in juxtaposition to a patient's head. To this end, the trough 30 substantially defines a U-shape about the patient's head 16. When used in a typical ophthalmic procedure, the trough 30 is located between a patient's head and a U-shaped wrist rest 18.

Due to the construction of the tab section 22b and its arrangement with respect to the trough 30, a natural drain from the area about eyes of the patient 12 is formed. This allows fluids to flow from the operative site to the trough 30 during ophthalmic procedures. Once in the trough 30, the fluids flow to the lowest portion thereof at which is located the port 50.

As is readily apparent, because the outlet of the port nozzle 50 is located on the underside of the drape 10, a non-sterile nurse can readily attach secondary equipment to the nozzle 50 without affecting the sterility of the operative site area. Accordingly, the trough 30 and the drape 10 provide for sterile removal of run-off fluids.

It can be appreciated that due to the gusset nature of the trough 30 (the gusset members 50 and 52 that define the trough 30), the trough 30 is easily collapsible to a flat state. Therefore, the drape 10 can be easily folded prior to use. Accordingly, the surgical drape 10 can be packaged in a compact folded form that can be readily unfolded by appropriate surgical personnel preparing the patient for surgery.

As discussed above, there is also provided in the tab section 22b of the minor sheet 20, a fenestration or window 40 that provides an incise area that is centered about the eyes of the patient 12. The fenestration 40, in the embodiment illustrated, is circumscribed by an adhesive layer 60. The adhesive layer 60 affixes the fenestration 40 in sealing relationship on an operative site of the patient. The adhesive layer 60 is preferably covered by a suitable protective cover to retain the tackiness of the adhesive and to prevent inadvertent adherence of the film during storage of the drape 10. When the drape 10 is to be used, the protective cover is removed so that the adhesive layer 60 can be affixed about the operative site in sealing relationship. Fluid such as irrigation fluid, will then drain from the operative site, down the side of the patient's head 16 onto the tab section 22b and then into the trough 30.

Other embodiments of the surgical drape of the present invention are possible. For example, the surgical drape can include a minor sheet portion on which the corners are eliminated. This provides for better draping and the elimination of excess drape that can get in the way of surgical personnel as they brush up against the drape.

Additionally, the minor sheet portion can include a large fenestration that registers about a patient's head. A larger incise area in the minor sheet portion allows the surgical drape to be used for different surgical procedures such as corrective rhinoplasty. A larger incise area also allows the drape to neck down on the patient's head creating a friction seal at the periphery of the surgical site.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A surgical drape comprising:
   a base sheet portion;
   a head covering sheet portion attached to the base sheet that covers at least a portion of a patient's head when the drape is placed on a patient, said head covering sheet including a slit to form a tab section having a convex periphery; and
   a fluid collection trough received within said slit of said head covering sheet portion.

2. The surgical drape of claim 1 wherein the head covering sheet portion is made of a translucent plastic film.

3. The surgical drape of claim 1 wherein the head covering sheet portion includes a fenestration that registers about a patient's eyes.

4. The surgical drape of claim 1 wherein the trough is contoured to conform about the patient's head.

5. The surgical drape of claim 1 including an outlet port operatively attached to the trough to permit extraction of fluid therefrom.

* * * * *